United States Patent [19]

Budzinski

[11] 4,266,063

[45] May 5, 1981

[54] PROCESS FOR PREPARING SUBSTITUTED PYRIDINYLOXY ETHER INTERMEDIATE

[75] Inventor: John C. Budzinski, West Chester, Pa.

[73] Assignee: E. I. Du Pont de Nemours and Company, Wilmington, Del.

[21] Appl. No.: 104,452

[22] Filed: Dec. 17, 1979

[51] Int. Cl.³ .............................................. C07D 213/64
[52] U.S. Cl. .................................... 546/302; 546/301
[58] Field of Search .......................................... 546/302

[56] References Cited

U.S. PATENT DOCUMENTS

| 4,046,553 | 9/1977 | Takahashi et al. | 546/300 |
| 4,083,714 | 4/1978 | Takahashi et al. | 71/94 |
| 4,092,151 | 5/1978 | Takahashi et al. | 71/94 |

Primary Examiner—Alan L. Rotman

[57] ABSTRACT

A process for preparing pyridinyloxyphenols, useful intermediates in preparing pyridyloxyphenyl ether herbicides, in which a halopyridine is heated with hydroquinone in the absence of base and, optionally, in the absence of solvent.

8 Claims, No Drawings

PROCESS FOR PREPARING SUBSTITUTED PYRIDINYLOXY ETHER INTERMEDIATE

BACKGROUND OF THE INVENTION

This invention relates to pyridinyloxyphenyl ether herbicides and, more particularly, to an improvement in a process for preparing pyridinyloxyphenol intermediates to such herbicides.

U.S. Pat. No. 4,046,553, to Takahashi et al discloses and claims the preparation of phenoxypyridine derivatives of Formula I

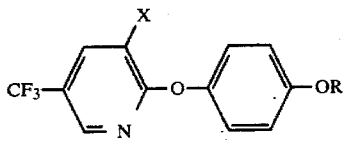

wherein X is H or Cl and R is H or a cation such as sodium, potassium, or ammonium. The compounds are prepared by reacting a 2-(Cl or F), 3-X, 5-CF$_3$-pyridine with hydroquinone or its mono alkyl ether in the presence of base at 70°-200° C. in the presence of a protic, apolar or ketonic solvent and then optionally dealkylating the reaction product according to Equation I.

EQUATION I

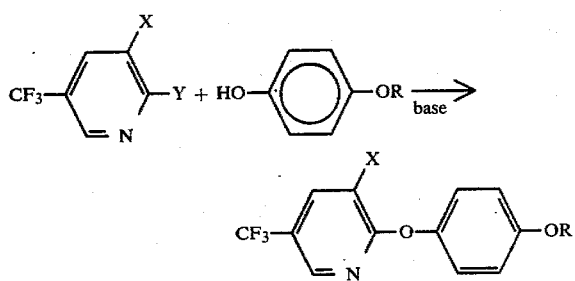

wherein
Y is F or Cl,
R is alkyl of 1 to 5 carbons, and
X is H or Cl.

Belgian Pat. No. 865,137 discloses and claims the preparation of 2-halo-5-trifluoromethyl pyridine derivatives which are useful as intermediates for pharmaceuticals, herbicides and dyes.

Belgian Pat. No. 862,325 relates to the preparation of compounds such as II.

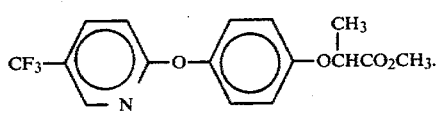

The following general reaction (Equation II) is disclosed for preparing intermediates to the above compounds:

EQUATION II

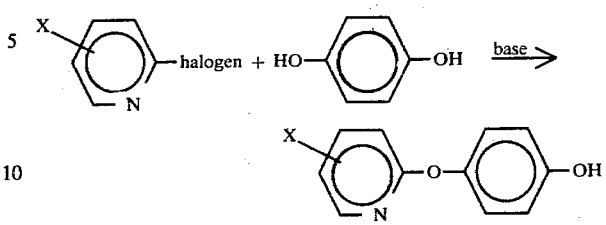

The production of hydroxydiaryl ethers of Formula III, wherein X, R and n have definitions of varying scope, by reaction of a halogenobenzene containing an active halogen atom or of 2- or 4-halogenopyridine, with a corresponding dihydroxybenzene in the presence of basic substance, particularly hydroxides and carbonates of alkali

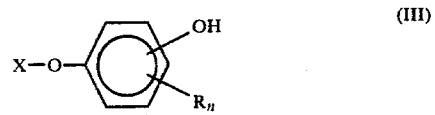

metals, in a polar aprotic solvent is known. The usefulness of this method of production is, however, impaired by the fact that there are formed, in addition to the desired hydroxydiaryl ethers of the Formula III varying amounts of diethers of the formula IV

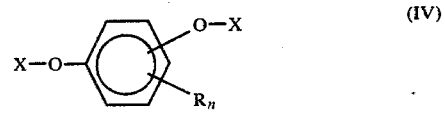

and in some cases these amounts are considerable. This necessitates an additional purifying operation in which the desired hydroxydiaryl ethers of Formula I have to be separated from the diethers of the above formula and from unreacted dihydroxybenzene.

In order to avoid the undesired formation of diethers it has been suggested to react halogenobenzenes having activated halogen with monoethers of dihydroxybenzenes, and to subsequently split off the protective group (see U.S. Pat. Nos. 2,926,093 and 3,240,706).

It has also been suggested that the formation of diethers occurring on reaction of halogenobenzenes with activated halogen and dihydroxybenzenes be avoided by using less than 1 mole, preferably less than 0.8 mole, of halogenobenzene per mole of dihydroxy compound and using per mole of dihydroxy compound 1 mole of alkali (see German Offenlegungsschrift No. 2,157,781).

It is also known to produce hydroxydiphenyl ethers by reaction of halogenobenzenes and a dihydroxybenzene in the presence of 2 moles of alkali per mole of dihydroxybenzene in a polar aprotic solvent (see German Offenlegungsschriften Nos. 2,433,066 and 1,911,799).

It is also known that 2-halogenopyridines can be reacted with hydroquinone in the presence of 1 to 1.2 moles of alkali per mole of hydroquinone to give pyridyl-2-oxy-4-hydroxyphenyl ethers (see German Offenlegungsschrift No. 2,546,251).

SUMMARY OF THE INVENTION

This invention provides a process for preparing pyridinyloxyphenols of Formula III.

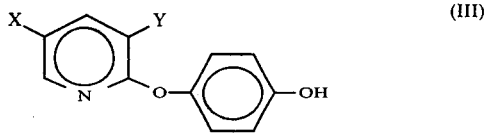

wherein
X is $CF_3$ or Cl; and
Y is H, Cl or Br;
provided that when X is Cl, Y is Cl or Br, and when X is $CF_3$, Y is H. According to the instant invention, a halopyridine is heated with hydroquinone in the absence of base and, optionally, in the absence of solvent according to the following reaction (Equation III).

EQUATION III

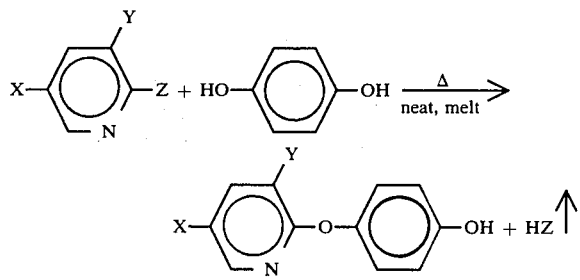

in which X and Y are as defined above and Z is Cl or Br. This invention is a signficant improvement over the prior art processes because the reaction does not require an equivalent of base. Moreover, the use of solvents is optional, and the production of dimeric by-products is inhibited. The compounds produced by the process of this invention are useful in preparing pyridinyloxyphenyl ether herbicides.

DETAILED DESCRIPTION OF THE INVENTION

According to the process of this invention, a halopyridine, such as 2-chloro-5-trifluoromethyl pyridine is heated with hydroquinone in the absence of base as shown by the following reaction (Equation IV).

EQUATION IV

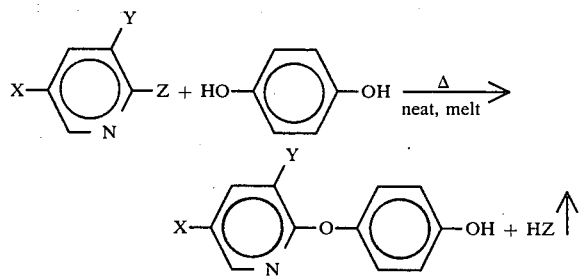

in which
X is $CF_3$ or Cl
Y is H, Cl or Br; and
Z is Cl or Br, provided that when X is Cl, Y is Cl or Br, and when X is $CF_3$, Y is H.

The temperature of the reaction is maintained in the range of about 100°–220° C., preferably in the range of 145°–170° C. If no solvent is used, it is preferable to run the reaction above the melt temperature of the mixture to allow intimate mixing.

The reaction mixture may be maintained in the above temperature range and the progress of the reaction may be monitored by any appropriate method (e.g., NMR). Using the preferred temperature range, the reaction time is 3–6 hours.

Pressure is not critical to the reaction, atmospheric being most convenient. The ratio of halopyridine to hydroquinone is also not critical, although ratios in the range of 1.2:1 to 1:1.2 provide ease of work-up of the resulting mixture and cost efficiency.

An inert solvent selected from the group consisting of toluene, xylene, chlorobenzene, o-dichlorobenzene, 1,1,1-trichloroethane, trichloroethylene, ethylbenzene also may be used, but this is not necessary. The reaction may also be run in the presence of the appropriate halogenated carboxylic acid derivative to be used in the final alkylation step for the preparaation of pyridinyloxyphenyl ethyl herbicides. Suitable halogenated carboxylic acid derivatives include: methyl 2-chloropropionate, ethyl 2-bromopropionate methyl-4-bromo-2-pentenoate and ethyl 4-chloro-2-pentenoate. The halogenated carboxylic acid derivative is inert under the conditions employed for the reaction and only takes place in the presence of base. When 2-bromo-5-trifluoromethylpyridine (where $X=CF_3$, $Y=H$ and $Z=Br$) is reacted with hydroquinone in the presence of a base such as potassium hydroxide, potassium carbonate or sodium hydride in the presence of a solvent such as DMSO, 2,2'-[1,4-phenylenedi(oxy)]bis[5-trifluoromethyl)-pyridine](V) was formed as the principal product.

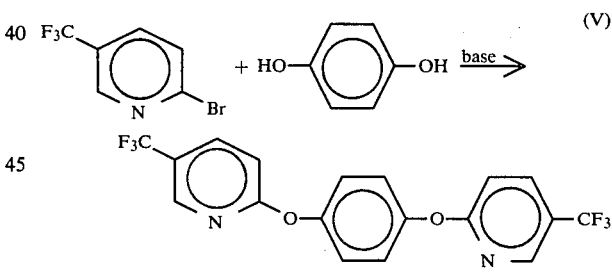

Similarly, when the reaction was run without solvent in the presence of potassium carbonate, 2,2'-[1,4-phenylenedi(oxy)]bis[5-(trifluoromethyl)-pyridine] (IV) was the principal reaction product.

When base is excluded from this reaction, 2,2'-[1,4-phenylenedi(oxy)]bis[5-(trifluoromethyl)-pyridine] (V) is formed only in small amounts, and the principal product is 4-[(5-trifluoromethyl)-pyridine-2-yloxy]phenol.

The following examples illustrate the reactions. Temperatures are in degrees Centigrade unless otherwise indicated.

EXAMPLE 1

Preparation of 2-chloro-5-trifluoromethyl pyridine from 6-chloronicotinic acid

A mixture of 200 g 6-chloronicotinic acid, 180 g of hydrogen fluoride and 348 g sulfur tetrafluoride was heated at 120° for 10 hours, with agitation in a bomb.

The mixture was then washed out of the bomb with methylene chloride and carefully poured into about 1 liter of ice water. It was then made basic with ammonium hydroxide. The mixture was extracted thoroughly with methylene chloride. This extract was washed with water, poured through a cotton plug then stripped at about 30° on a rotary evaporator to give an oil; yield=165 g. This oil was purified by partial crystallization in an ice bath to give 89 g of solid
m.p. 25°–30°; b.p. 147°.

NMR CDCl$_3$, 7.90$\delta$, d, J=12 Hz, 1H; 8.33$\delta$, dd, J=12, 2 Hz, 1H; 9.15$\delta$, d, J=2 Hz, 1H.

EXAMPLE 2

Preparation of 4-[(5-trifluoromethyl)pyridine-2-yloxy]phenol

A mixture of 14 g hydroquinone and 18 g 2-chloro-5-trifluoromethyl pyridine was heated with stirring under N$_2$ at 150°–160° for a total of 8 hours. Thin-layer chromatography showed that only a trace of 2-chloro-5-trifluoromethyl pyridine remained. The melted mixture was poured into water with rapid stirring. The resulting gummy mass was triturated with water, then separated and dissolved in about 150–200 ml diethyl ether. To the ether solution was added 40 ml of 50% NaOH along with about 20 g of ice. The mixture was agitated until a flocculant precipitate formed which was then collected and washed with ether and acetone. The solid cake was then suspended in water and the mixture made acidic with 10% hydrochloric acid. The resulting solid was collected and dried; yield=17 g.

NMR CDCl$_3$, 7.1–7.4$\delta$, mult, 6H; 8.35$\delta$, dd, J=10, 2 Hz; 8.90$\delta$, br s, 1H.

This product could be purified by silica gel chromatography to give a pure material m.p. 84°–87° or used directly in subsequent reactions without further purification.

By using the general procedure described in Example 2 and the appropriately substituted pyridine, the preparation of 4-(3,5-dichloro-2-pyridinyloxy)-phenol can be accomplished.

EXAMPLE 3

Preparation of Methyl 4-[4-[5-(trifluoromethyl)-2-pyridinyloxy]phenoxy]-2-propanoate from hydroquinone, 2-chloro-5-trifluoromethyl pyridine and methyl 2-bromopropanoate mixtures A mixture of 3.3 g hydroquine 5.4 g 2-chloro-5-trifluoromethyl pyridine and 10 ml methyl 2-bromopropanoate was refluxed a total of 11 hours. To this mixture was added 2.0 g potassium carbonate. Refluxing was continued for 1 hour and then the hot mixture was poured in water, made basic with sodium hydroxide and extracted with diethyl ether. The ether was dried (MgSO$_4$) and then stripped on a rotary evaporator at 90°–100° to give a residual oil; yield=5.5 g of product, identical to the material of Example 3.

2-Bromo-5-trifluoromethyl pyridine can be used in place of the 2-chloro-5-trifluoromethyl pyridine in the above procedures with minor modifications.

EXAMPLE 4

Methyl 4-[4-[5-(trifluoromethyl)-2-pyridinyloxy]phenoxy]-2-pentenoate

In 50 ml of methyl ethyl ketone, 2.0 g (0.0078 mole) of 4-[5-(trifluoromethyl)-2-pyridinyloxy]phenol, 3.2 g of methyl 4-bromo-2-pentenoate, and 2.0 g of potassium carbonate were refluxed with constant stirring for 32 hours. Upon cooling to room temperature, the suspension was filtered through celite and the insoluble material washed with 75 ml of acetone. The filtrate was concentrated under reduced pressure to give an oily residue which was dissolved in 125 ml of ethyl ether and transferred to a separatory funnel. After washing with saturated sodium bicarbonate and water, the ether layer was dried over magnesium sulfate and charcoal filtered. Under reduced pressure, the solvent was evaporated and traces of volatile impurities removed at 0.4 mm Hg. (50° for 2 hours) to yield 2.4 g (84%) of product, N$_D^{25}$ 1.520.

IR (neat): 5.75 (CO$_2$CH$_3$), 5.95, 6.15 (C=C), 6.55, 6.65, 11.85 microns; NMR (CDCl$_3$): $\delta$ 1.50 (d, 3H, CH$_3$, J=7 Hz), 3.75 (s, 3H, OCH$_3$), 4.70–5.20 (m, 1H, allylic hydrogen), 5.90–6.30 (m, 1H, vinylic hydrogen), 6.80–7.35 (m, 5H, vinylic proton and phenol protons), 7.80–8.10 (m, 2H, pyridine protons), 8.40–8.60 (m, 1H, pyridine proton); mass spectrum: (m/e): M+367 (m.w. 367).

EXAMPLE 5

Methyl 4-[4-(3,5-dichloro-2-pyridinyloxy)phenoxy]-2-pentenoate

To 2.5 g (0.0098 mole) of 4-(3,5-dichloro-2-pyridinyloxy)phenol, and 1.5 g of potassium carbonate in 40 ml of methyl ethyl ketone, 2.5 g of methyl 4-bromo-2-pentenoate, dissolved in 10 ml of methyl ethyl ketone, was added at room temperature with constant stirring. The mixture was heated at reflux for 20 hours. Upon cooling to room temperature, the mixture was filtered through celite and the insoluble material washed with 50 ml of ethyl ether. An oily residue which remained after concentrating the filtrate under reduced pressure was dissolved in 125 ml of ethyl ether and washed with excess water. Drying over magnesium sulfate, charcoal filtering, and removal of solvent and volatile impurities at reduced pressure (0.35 mm Hg, 1.5 hours at 75°) gave 2.5 g (69%) of product, N$_D^{25}$ 1.5790.

IR (neat): 5.75 (CO$_2$CH$_3$), 5.95, 6.30 (C=C), 6.60, 6.90, 11.95 microns; NMR (CDCl$_3$): $\delta$ 1.50 (d, 3H, CH$_3$, J=7Hz), 3.75 (s, 3H, OCH$_3$), 4.75–5.15 (m, 1H, allylic hydrogen), 5.85–6.20 (m, 1H, vinylic proton), 6.70–7.20 (m, 5H, vinylic proton and phenol protons), 7.60–7.90 (m, 2H, pyridine protons).

What is claimed is:

1. A process for preparing a compound of the formula

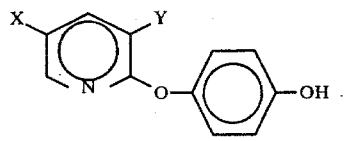

which consisting essentially of heating a substituted pyridine of the formula

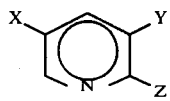

wherein X is $CF_3$ or Cl, Y is H, Cl, or Br and Z is Cl or Br, provided that when X is Cl, Y is Cl or Br, and when X is $CF_3$, Y is H, with hydroquinone in the absence of a base at a temperature in the range of about 100°–220° C. in the presence or absence of a solvent.

2. The process of claim 1 in which the ratio of substituted pyridine to hydroquinone is 1.2:1 to 1:1.2.

3. The process of claims 1 or 2 in which the substituted pyridine is heated with hydroquinone in the presence of an inert solvent selected from the group consisting of toluene, xylene, chlorobenzene, o-dichlorobenzene, 1,1,1-trichloroethane, trichloroethylene, tetrachloroethylene and ethylbenzene.

4. The process of claims 1 or 2 which is carried out in the neat melt base.

5. The process of claims 1 or 2 in which the substituted pyridine is heated with hydroquinone in the presence of a lower alkyl 2-chloro- or 2-bromopropionic ester.

6. The process of claims 1 or 2 in which the substituted pyridine is heated with hydroquinone in the presence of a lower alkyl 4-chloro- or 4-bromo-2-pentenoic ester.

7. The process of claim 1 in which X is Cl, Y is Cl and Z is Cl.

8. The process of claim 1 in which X is $CF_3$, Y is H and Z is Cl.

* * * * *